United States Patent
Sliwa et al.

(10) Patent No.: US 8,545,408 B2
(45) Date of Patent: Oct. 1, 2013

(54) COMBINATION CATHETER FOR FORWARD AND SIDE LESIONING WITH ACOUSTIC LESION FEEDBACK CAPABILITY

(75) Inventors: John Sliwa, Los Altos Hills, CA (US); Zhenyi Ma, San Jose, CA (US); Stephen Morse, Menlo Park, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 266 days.

(21) Appl. No.: 13/113,170

(22) Filed: May 23, 2011

(65) Prior Publication Data
US 2012/0302882 A1 Nov. 29, 2012

(51) Int. Cl.
*A61B 8/00* (2006.01)

(52) U.S. Cl.
USPC ............................................ 600/439; 606/32

(58) Field of Classification Search
USPC ....................................................... 600/439
See application file for complete search history.

(56) References Cited

U.S. PATENT DOCUMENTS

| | | | |
|---|---|---|---|
| 5,588,432 A | 12/1996 | Crowley | |
| 2009/0131798 A1 | 5/2009 | Minar et al. | |
| 2010/0168569 A1 | 7/2010 | Sliwa et al. | |
| 2010/0168570 A1 | 7/2010 | Sliwa et al. | |
| 2010/0168572 A1 | 7/2010 | Sliwa et al. | |
| 2012/0265192 A1* | 10/2012 | Sliwa et al. | 606/33 |

FOREIGN PATENT DOCUMENTS

| | | |
|---|---|---|
| EP | 1 554 986 A1 | 7/2005 |
| WO | 2010082146 A1 | 7/2010 |
| WO | 2010103423 A2 | 9/2010 |

OTHER PUBLICATIONS

M. Wright et al., "Real-time lesion assessment using a novel combined ultrasound and radiofrequency ablation catheter", Heart Rhythm, Feb. 2011, 9 pp., vol. 8, No. 2, Elsevier Inc.

* cited by examiner

*Primary Examiner* — Jonathan Cwern
(74) *Attorney, Agent, or Firm* — Mattingly & Malur, PC

(57) ABSTRACT

An ablation system comprises a catheter including a pulse-echo ultrasonic transducer disposed in a distal portion and arranged to emit and receive an acoustic beam. The transducer emits and receives acoustic pulses to provide transducer detected information regarding the targeted tissue region being ablated. A rotation mechanism rotates at least the distal portion around a longitudinal axis of the catheter. A control and interface system processes the transducer detected information and provides feedback to a user via a user interface and/or the control and interface system to be used to control ablation. The transducer detected information includes a detected lesion depth along a beam emanation direction. The control and interface system includes a lesion depth correction module which converts the detected lesion depth along the beam direction to a corrected lesion depth in a normal direction which is perpendicular to the tissue surface in contact with the ablation element.

31 Claims, 6 Drawing Sheets

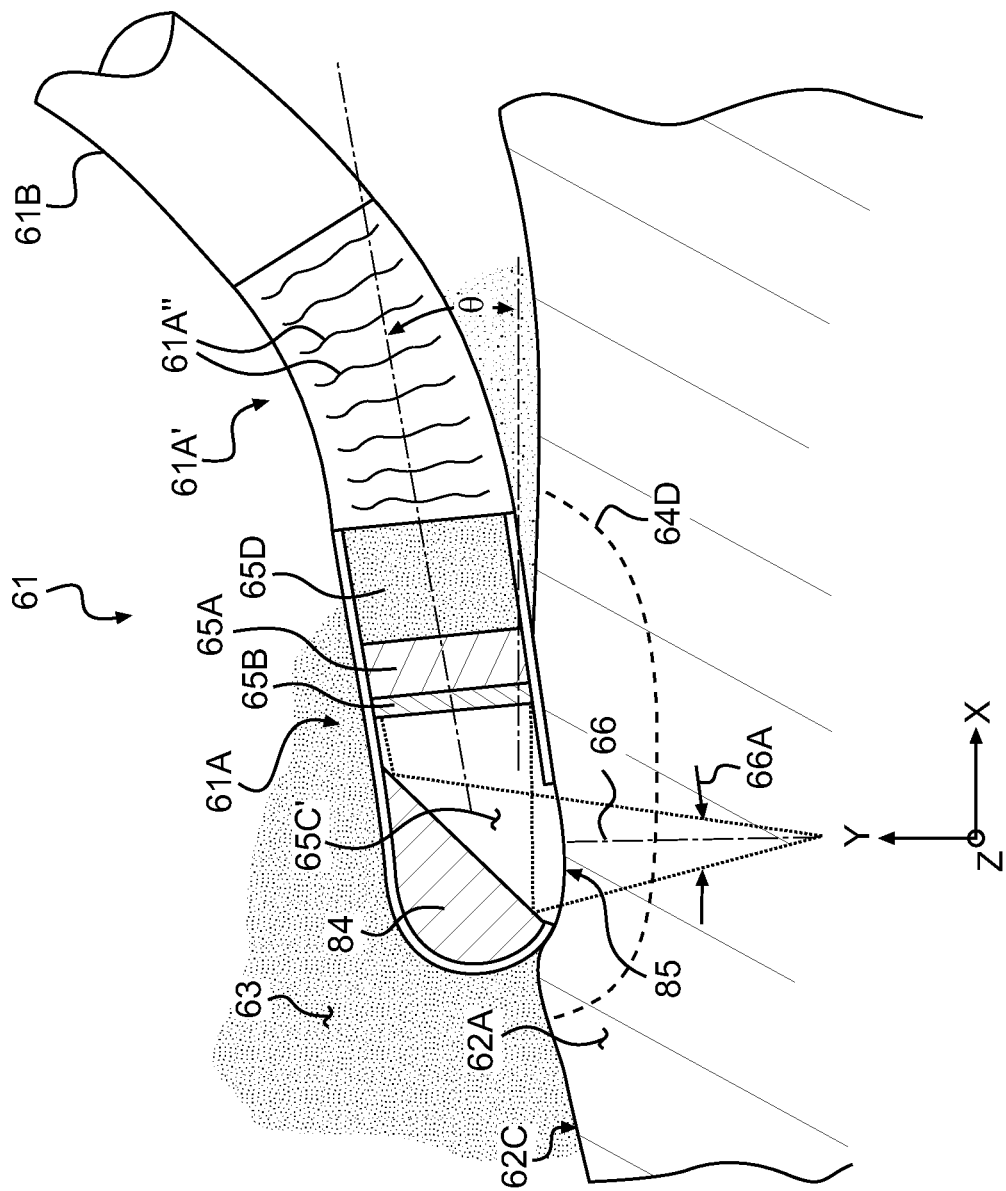

COMBINATION CATHETER FOR FORWARD AND SIDE LESIONING WITH ACOUSTIC LESION FEEDBACK CAPABILITY

BACKGROUND OF THE INVENTION

The present invention relates generally to ablation devices and, more specifically, to a combination catheter for forward and side lesioning with acoustic or ultrasonic lesion feedback capability.

Current industry R&D in ultrasonic lesion feedback focuses on transducers that look out from the ablation electrode tip both forwardly and sideways. This requires the use of dual transducers in an ablation instrument such as a catheter, resulting in a considerable expense and a significant loss of electrode tip metal for RF (radiofrequency) ablation or the like. Such an approach leads to an undesirably larger tip size to accommodate the two transducers or to poorer performing smaller (thinner) acoustic standoffs and/or backers for the dual transducers.

BRIEF SUMMARY OF THE INVENTION

Embodiments of the present invention provide a combination catheter for forward and side lesioning with acoustic or ultrasonic lesion feedback capability.

In accordance with an aspect of the present invention, an ablation system comprises: a catheter including an elongated catheter body extending longitudinally between a proximal end and a distal end along a longitudinal axis, and at least one ablation element disposed in a distal portion which is adjacent the distal end of the catheter body to ablate a targeted tissue region outside the catheter body by contacting a tissue surface; a pulse-echo ultrasonic transducer disposed in the distal portion and arranged to emit and receive an acoustic beam having a centroid along a beam axis direction at an angle of between about 0 degree and about 90 degrees relative to a distal direction of the longitudinal axis at a location of intersection between the longitudinal axis and the beam direction of the centroid of the acoustic beam, wherein the pulse-echo ultrasonic transducer emits and receives acoustic pulses to provide transducer detected information regarding the targeted tissue region being ablated; a rotation mechanism to rotate at least the distal portion around the longitudinal axis; and a control and interface system to process the transducer detected information from the pulse-echo ultrasonic transducer and to provide feedback to at least one of a user via a user interface or the control and interface system itself to be used to control ablation by the at least one ablation element. The transducer detected information includes a detected lesion depth along a beam emanation direction. The control and interface system includes a lesion depth correction module which converts the detected lesion depth along the beam direction to a corrected lesion depth in a normal direction which is perpendicular to the tissue surface in contact with the at least one ablation element.

In some embodiments, the acoustic beam passes into the targeted tissue region from the pulse-echo ultrasonic transducer facing the targeted tissue region in a transducer-facing direction, the acoustic beam has a beam-emanation direction from the pulse-echo ultrasonic transducer, and the beam-emanation direction is same as the transducer-facing direction. An acoustic minor redirects the acoustic beam from the pulse-echo ultrasonic transducer into the targeted tissue region at a beam-emanation direction. The pulse-echo ultrasonic transducer faces the acoustic minor in a transducer-facing direction. The beam-emanation direction is different from the transducer-facing direction. The transducer-facing direction is substantially along the longitudinal axis of the distal portion of the catheter and the beam-emanation direction is at an angle relative to the transducer-facing direction. The distal portion has a rigid part. The distal portion has a flexible part coupled between the rigid part and a proximal portion of the elongated catheter body.

In specific embodiments, the rotation mechanism rotates the catheter body including the distal portion as a whole, the rotation being one of manual or robotic or automatic rotation. The rotation mechanism rotates the distal portion relative to a proximal portion of the catheter body, the rotation being one of manual or robotic or automatic rotation. The system further includes a sheath through which the catheter body is introduced to the targeted tissue region, and the rotation mechanism rotates one of the distal portion or the catheter body including the distal portion with respect to the sheath.

In some embodiments, the lesion depth correction module is configured to convert the detected lesion depth along the beam direction to the corrected maximum lesion depth using both (i) a measured or observed tissue contact angle between the tissue surface in contact with the distal portion and the longitudinal axis of the distal portion of the catheter body and (ii) a model or stored description of lesion shapes made under similar ablating conditions using the at least one ablation element, wherein the tissue contact angle is provided by one of: receiving from a user a visual estimation of the angle; deriving the angle from an imaging modality for imaging position and orientation of the distal portion; deriving the angle from a three-dimensional surface modeling system to provide spatial orientation of the distal portion and spatial map and shape of the tissue surface; and deriving the angle from a contact angle sensor in or adjacent the distal portion. The model or stored description of lesion shapes, which is obtained based on multiple combination of at least two of RF power, RF time, tissue contact angle, and irrigant flow rate, provides a nominally expected lesion shape and size as described by at least one of a maximum depth, a maximum width, a maximum length, or a volume of the lesion. The nominally expected lesion shape is size scaled, using a ratio of the detected lesion depth along the beam direction and a corresponding depth of the nominally expected lesion shape along the beam direction, to obtain a size-scaled lesion shape having the corrected maximum lesion depth. The lesion depth correction module also provides one or more of the maximum length, the maximum width, and the volume of the lesion of the size-scaled lesion shape.

In specific embodiments, a robot is coupled to the catheter and the rotation mechanism to manipulate the catheter. The control and interface system is coupled to the robot to control the robot using the transducer detection information. The rotation mechanism comprises a proximal catheter handle coupled with the catheter body and the distal portion. The transducer angle is between about 30 and about 60 degrees. The transducer angle may be about 45 degrees. An ablative energy source supplies ablative energy to the at least one ablation element, the ablative energy source comprising one or more of unipolar RF, bipolar RF, microwave, laser, cryo, infrared, electroporation, and chemicals. The pulse-echo ultrasonic transducer has an operating frequency of between about 3 megahertz and about 60 megahertz.

In some embodiments, the control and interface system is coupled to the pulse-echo ultrasonic transducer to operate the transducer to perform transducer detection at least one of: before supplying ablative energy to the at least one ablation element; simultaneously with supplying ablative energy to the at least one ablation element; while the at least one ablation element is inactive and for time periods that are time-interleaved with supplying ablative energy to the at least one ablation element; after supplying ablative energy to the at least one ablation element and stopping supply of the ablative energy; and for multiple acoustic feedback detections over a period of a heartbeat or breath; for at least one acoustic detection made in a timed relationship with a heartbeat cycle or ECG signal.

In specific embodiments, the control and interface system is coupled to the pulse-echo ultrasonic transducer to operate the transducer to have a duty cycle of less than about 20%. The control and interface system is coupled to the pulse-echo ultrasonic transducer to operate the transducer to provide an on-time for an ultrasonic measurement period that is approximately equal to or less than a thermal time constant of the targeted tissue region with the tissue surface being contacted by the at least one ablation element during cooling of the targeted tissue region. The control and interface system is coupled to the pulse-echo ultrasonic transducer to operate the transducer to provide an on-time for an ultrasonic measurement period that is less than about 0.15 seconds.

In some embodiments, processing the transducer detection information by the control and interface system comprises at least one of: determining the corrected lesion depth; determining lesion-making progress; determining a tissue thickness; determining lesion transmurality; identifying activity indicative of prepopping or popping; determining a rotation state of the distal portion; determining a distance from the distal portion to the tissue surface from within a blood pool.

In specific embodiments, the control and interface system is coupled to the rotation mechanism to rotate the distal portion in order to achieve a maximal degree of orthogonality with respect to the tissue surface. The system further comprises one of an acoustic standoff and a lens disposed between the pulse-echo acoustic transducer and the targeted tissue region. The system further comprises an attenuative backer material having a shape conducive to reflection minimization, and the pulse-echo acoustic transducer is disposed between the attenuative backer material and the targeted tissue region. The pulse-echo acoustic transducer is mounted in a hole in the distal portion and the distal portion comprises an electrically conductive material at least on a surface of the distal portion to deliver RF ablation at least from outside of a region of the transducer beam path. The pulse-echo acoustic transducer is the only acoustic transducer in the catheter. The control and interface system is coupled to the rotation mechanism to rotate the distal portion and to the distal portion to manipulate other movements of the distal portion in order to orient the beam direction to form an angle of between about 0 and about 45 degrees relative to the tissue surface in contact with the at least one ablation element.

These and other features and advantages of the present invention will become apparent to those of ordinary skill in the art in view of the following detailed description of the specific embodiments.

BRIEF DESCRIPTION OF THE DRAWINGS

FIG. 7 is a partial sectional view of an RF ablation tip wherein the transducer itself is forward pointing but its beam is redirected sideways by an acoustic minor before exiting the ablation tip.

DETAILED DESCRIPTION OF THE INVENTION

Figure 1:
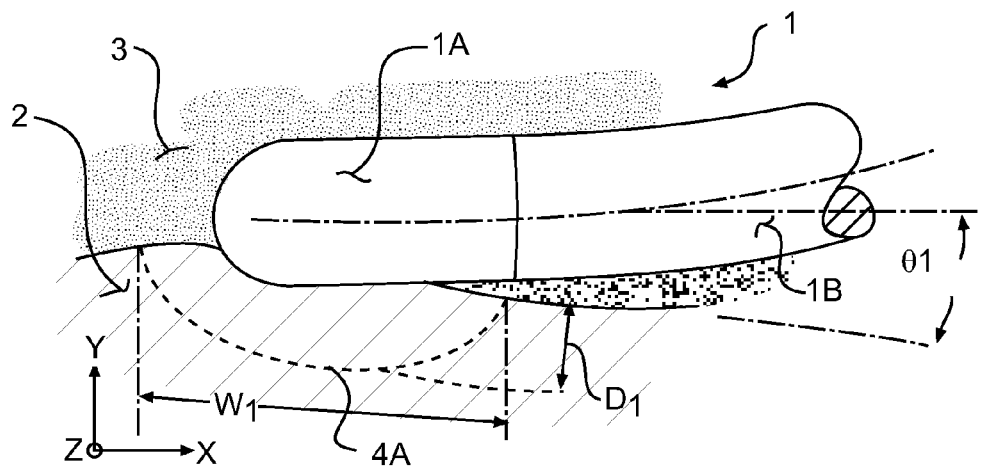
FIG. 1 shows an example of sideways ablation using an ablating catheter in a sideways manner to lesion tissue from within a blood cavity or heart chamber.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Furthermore, some portions of the detailed description that follow are presented in terms of algorithms, flow-charts and symbolic representations of operations within a computer. These algorithmic descriptions and symbolic representations are the means used by those skilled in the data processing arts to most effectively convey the essence of their innovations to others skilled in the art. An algorithm is a series of defined steps leading to a desired end state or result which can be represented by a flow chart. In the present invention, the steps carried out require physical manipulations of tangible quantities for achieving a tangible result. Usually, though not necessarily, these quantities take the form of electrical or magnetic signals or instructions capable of being stored, transferred, combined, compared, and otherwise manipulated. It has proven convenient at times, principally for reasons of common usage, to refer to these signals as bits, values, elements, symbols, characters, terms, numbers, instructions, or the like. It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing," "computing," "calculating," "determining," "displaying," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

The present invention also relates to an apparatus for performing the operations herein. This apparatus may be specially constructed for the required purposes, or it may include one or more general-purpose computers selectively activated or reconfigured by one or more computer programs. Such computer programs may be stored in a computer-readable storage medium, such as, but not limited to optical disks, magnetic disks, read-only memories, random access memories, solid state devices and drives, or any other types of media suitable for storing electronic information. The algorithms and displays presented herein are not inherently related to any particular computer or other apparatus. Various general-purpose systems may be used with programs and modules in accordance with the teachings herein, or it may prove convenient to construct a more specialized apparatus to perform desired method steps. In addition, the present invention is not described with reference to any particular programming language. It will be appreciated that a variety of programming languages may be used to implement the teachings of the invention as described herein. The instructions of the programming language(s) may be executed by one or more processing devices, e.g., central processing units (CPUs), processors, or controllers.

Exemplary embodiments of the invention, as will be described in greater detail below, provide acoustic or ultrasonic lesion feedback RF ablators and ablator tips and, more specifically, to an ablation system that employs an ultrasonic transducer with an angular orientation for lesion feedback in an ablation catheter, preferably converts a detected lesion depth from the ultrasonic transducer to a corrected lesion depth, and utilizes the lesion feedback to control and/or report the progress of the ablation.

An ideal lesion-feedback capable ablation catheter would be small in size (e.g., 7 French) and allow for lesions to be made forwardly or sideways (or in-between tip-to-tissue orientations) with the aid of lesion feedback information. In specific embodiments, a single (only one) transducer catheter is provided for that purpose. Prior work involved dual transducers on 9 French catheters, one transducer being forward looking and the other one side-looking. The single acoustic transducer herein is still a pulse-echo pinger device. Dual transducers may be used in other embodiments.

FIG. 1 shows an example of sideways ablation using an ablating catheter 1 in a sideways manner to lesion tissue 2 from within a blood cavity or heart chamber 3. In this mostly side-burning approach, the longitudinal axis of the ablating tip 1a has an approximate angle $\theta_1$ with the tissue wall 2. The tissue contact angle $\theta_1$ in this side-burning scenario is typically between about 0 and 45 degrees. A lesion 4a is depicted as having been formed and that lesion 4a is shown as having an approximate maximum depth of $d_1$ and an approximate maximum length (along the tip 1a) of $w_1$. As is usually the case, the catheter 1 has a metallic or electrically conductive ablative RF electrode tip 1a and an extended flexible shaft or lumen 1b.

Figure 2:
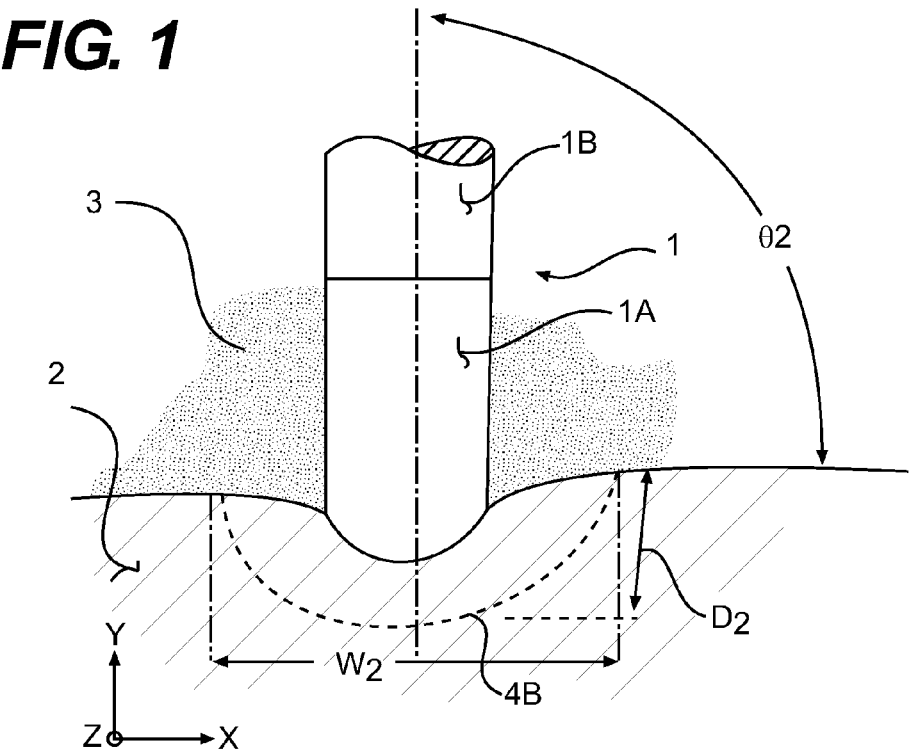
FIG. 2 shows an example of forward tip-end ablation.

FIG. 2 shows an example of forward tip-end ablation. The catheter 1 is essentially the same as that in FIG. 1 but it is positioned to have a tissue contact angle $\theta_2$ that is generally between about 45 and 90 degrees for forward or tip burning. A formed lesion 4b is shown as having a different maximum depth $d_2$ and different maximum width $w_2$ as compared to those dimensions in FIG. 1.

Both FIG. 1 and FIG. 2 have XYZ coordinate systems. The X-axis is parallel to the longitudinal axis of the catheter tip 1a at a zero-degree tissue contact angle, and the Y-axis is parallel to the longitudinal axis of the catheter tip 1a at a 90-degree tissue contact angle. In the sideways ablation case of FIG. 1, the lesion 4a will be longer along the tip direction ($w_1$ direction along X-axis) than it is wide (along the Z-axis). This is simply because the tip-to-tissue contact area is longer in that direction. In the forward ablation case of FIG. 2, the lesion width $w_2$ will actually approximate a constant radius (presuming $\theta_2$ is anywhere near 90 degrees as depicted). In any case lesion 4b of FIG. 2 will typically be rotationally symmetric to the Y axis even if the lesion radius isn't constant. This is simply because of the rotational symmetry of the contacting tip.

Figure 3:
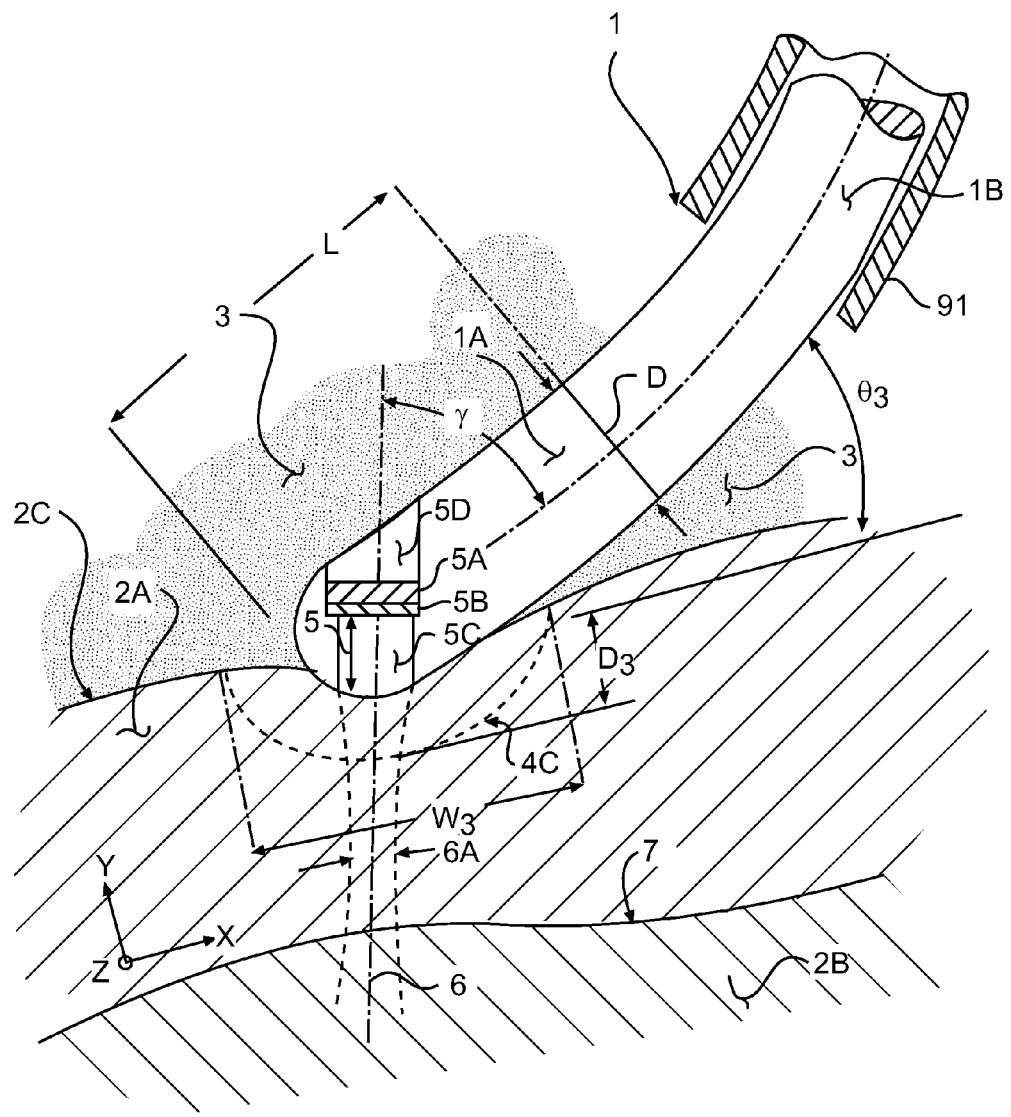
FIG. 3 is a partial sectional view of an RF ablation tip having a single transducer with an angular orientation for lesion feedback during tissue ablation.

FIG. 3 shows an RF ablation electrode tip having a single ultrasonic transducer with an angular orientation to its surrounding ablator electrode tip for acoustic lesion feedback during tissue ablation. An RF ablation catheter 1 includes a distal ablating electrode tip 1a connected proximally to a catheter body 1b which is flexible and has one or more interior lumens. In this example, the catheter 1 is depicted immersed within a blood pool 3 for forming a lesion 4c on and into an endocardial wall 2c of endocardial tissue 2a. The thermal RF lesion 4c is formed on and into the tissue wall 2c by the catheter electrode RF tip 1a. A single ultrasonic transducer includes a piezomaterial 5a and preferably one or more acoustic matching layers 5b. The ultrasonic transducer is mounted in the tip 1a at a transducer beam centroid angle $\gamma$ to the tip axis, which is between about 30 and about 60 degrees, preferably about 45 degrees (as depicted), relative to the forward direction of the tip longitudinal axis of the tip 1a. The ablating electrode tip 1a is typically formed, as is widely practiced, from a metal such as a platinum, gold or rhodium alloy and herein is shown drilled out or bored in order to accept the transducer and allow unobstructed acoustic beam emanation from the tip 1a. The acoustic beam which emanates has a centroid 6 and a beam envelope 6a. The drilled out portion of tip 1a directly in the beampath may optionally be later overcoated with thin film electrically conductive metal such that RF lesioning still happens everywhere the tip touches the tissue 2c. Alternatively, the bored out beampath region is not relied upon for RF ablation and only the surrounding remaining tip metal still serves to cause RF ablation. Typically the tip 1a starts as a solid cylinder of metal which is bored out however within the scope is a tip which starts as a tube or shell. A sheath 91 may be used to introduce the catheter 1 to the target tissue region for ablation. As known in the art, the sheath 91 is typically made of a polymeric material and may be braided, and may be steerable or non-steerable. As discussed below, the catheter 1 may be rotated relative to the non-rotating sheath 91 which serves to protect the patient's lumen such as an artery or vein during introduction and/or rotation of the catheter 1.

The entire catheter tip 1a is further depicted having a presentation to tissue angle (tissue contact) of $\theta_3$ relative to the endocardial wall 2c, which is horizontal along axis X in FIG. 3. The transducer 5a/5b emits and receives outgoing and incoming reflected acoustic pulses traveling at the tissue's approximate sonic velocity of 1540 meters/sec along a beam axis 6 within a beam envelope 6a. The transducer 5a/5b, as is customary, is mounted on an acoustically attenuative backer material 5d. The acoustic waves travel through the lesion 4c outwards and then back inwards as they are reflected from various depths in accordance with lesion induced damage and microbubbles at each such depth. The lesion 4c has a depth $d_3$ measured along the acoustic beam path 6 which just happens to also be the maximum penetration depth of the lesion into tissue 2a for this particular tip $\theta_3$. Note that for randomly chosen tip-to-tissue angles the "detected" acoustic depth will not be "straight into" the tissue and therefore may somewhat different than the actual maximum "straight down" depth. Again we emphasize that the beam envelope 6a typically has a finite width which converges or diverges with distance from the transducer, but the beam will always have at least one centroid 6 or central angle or sort of centerline with an angle $\gamma$ to the local axial tip axis. This centroid may be defined in any conventional manner such as its being an axis of beam symmetry or an axis of peak intensity.

FIG. 3 shows an underlying untargeted tissue layer 2b under the tissue layer 2a to be ablated. This is to call attention to the fact that the transducer 5a/5b may also detect interfaces such as the 2a/2b interface. A likely real example would be endocardial tissue 2a and underlying pericardial tissue 2b. As the heart oscillates and the blood surges there through, there usually is a heartbeat-time angular excursion of the tissue contact angle $\theta_3$. By time-sampling the pinged depths across multiple heartbeats and knowing the tip-to-tissue contact angles, one can determine the shortest distance (true local thickness) of layers such as 2a/2b by simple trigonometry. That information can be utilized to compute a degree of transmurality of the lesion 4c in layer 2a or to determine a safe distance from an esophagus, lung or aorta 2b to be avoided, for example.

Furthermore, one may utilize transducer pinging to monitor the approach of the catheter tip to the wall 2c from within the blood pool 3 or to detect incipient (inaudible prepops) or actual steam pops and avoid large pops by throttling back or shutting off ablation power and/or increasing nearfield cooling irrigation. One may also deduce the angle of the tip relative to the wall before contact since the tip motions provide some angularly swept data; however, in a preferred approach as discussed below, techniques involving the use of navigational systems such as Ensite™ or Carto™, or the use of X-ray or the like can be utilized to obtain tip angle $\theta_3$ to tissue surface 2c.

It will be appreciated that if $\gamma$ and $\theta_3$ are both 45 degrees, then the beam 6a of the transducer 5a/5b will be oriented normally or at 90 degrees into the tissue wall 2c (along the -Y axis) in FIG. 3. More typically though, $\gamma$ will be fixed at an angle of about 45 degrees (typically between 30 and 60 degrees) and $\theta_3$ will be variable throughout an ablation procedure and will depend on how the catheter tip 1a is presented to the tissue wall 2c by the practitioner for that particular lesion. The presentation angle of the electrode tip 1a to tissue $\theta_3$ can physically be from about 90 degrees (tip-normal) to about 0 degree (tip-parallel) depending on the particular lesion being made. An ablation procedure may involve multiple lesions made at different contact angles. The tip may also be dragged during ablation as is known and the inventive feedback likewise gathered during such ablating/dragging.

Before proceeding note that in FIG. 3 the depicted lesion depth d3 is the maximum penetration depth of the lesion 4c measured orthogonal to the tissue surface 2c. If the lesion 4c is not hemispherical (i.e., not constant radius) in volumetric shape, then any different d measured along a beamline 6 which is not orthogonal into tissue 2c will have a depth (or radius) different from d-max. Practitioners are interested in d-max because it is the indicator for transmurality through the target layer 2c (the deepest lesion penetration). Most real lesions, depending on the tip angle $\theta_3$, will have fairly reproducible nonhemispherical shapes if not asymmetric shapes. Knowing this, one can either (a) use the non-orthogonally detected d as an approximation of d-max, or (b) utilize lookup tables or mathematical models of lesions, wherein based on a given depth (radius) along a first direction, one can compute the depth along a second direction (e.g., the orthogonal d-max direction). For maximal convenience, these models can utilize lesions of constant shape (fixed aspect ratios) which simply grow or scale in absolute size at those fixed ratios. In the unique case where the tissue contact angle $\theta_3$ is 45 degrees and the transducer 5a/5b is also mounted in the tip 1a at 45 degrees ($\gamma$=45 degrees), the pinged lesion depth $d_3$ is the actual tissue-orthogonal maximum penetrating lesion depth $d_3$ (because the transducer 5a/5b is orthogonal to the tissue 2c) and the maximum depth typically occurs directly or nearly directly under the most deeply tissue-indenting contacting tip portion. However, presuming the transducer angle $\gamma$ still is equal to 45 degrees (the same catheter) but the tissue contact angle $\theta_3$ is reduced to 30 degrees (from 45 degrees), the beam 6 centroid is no longer normal to the tissue 2c but is now oriented 15 degrees to it (not shown). If one knows the tip-tissue contact angle and has the lesion model for that tip angle then the maximum actual depth is easily computed by scaling the model to have the detected dimension along the detected direction and computing the depth along the orthogonal direction using the scaled model.

For a catheter tip 1a embedded, indented or depressed into a tissue surface 2c (as shown in FIG. 3) and for a reasonably wide range of angles $\theta_3$ (the variable tip tissue contact angles), the detected lesion depth $d_3$ is an approximation of the maximum depth when $\gamma$ (the fixed transducer angle) is fixed somewhere between about 30 and 60 degrees (preferably at about 45 degrees). Practitioners are typically interested in the maximum lesion depth for transmurality and in the lesion width/length insofar as being able to say adjacent lesions are continuous or abutted or not. Thus, depending on the required accuracy, the practitioner may want to utilize an inventive device having true d-max computation or lookup capability using the above-described angle-detection and lesion models.

The ablative tip 1a has an axial length of L and a diameter D. For a 7 French tip, D is 7/$\pi$ or 7 French divided by 3.1416 (just over 2 mm diameter). The tip length L will typically be in the range of about 2D to 6D presuming a rigid tip. 7-French devices are preferred for many ablations; however, the inventive devices may comprise any smaller or larger French size desired (e.g., 5 or 6 or 8 French).

Despite this fairly good depth approximation capability, it is actually possible to do even better if one knows the actual real-time tissue contact angle $\theta_3$ at the moment of measurement. In that case, one can apply a correction factor, if worthwhile, to account for differences between the detected depth and the actual maximum depth based on bench studies done using that tip orientation. This correction factor corrects for the fact that the "depth" measured along the acoustic beam line will typically be slightly non-normal to tissue and may report a "depth" which is actually larger for flat pancake lesions (or even smaller for narrow deep lesions) than the real 90 degree penetration depth.

The tissue contact angle $\theta_3$, if it is desired for the most accurate result, can be determined or deduced in one or more of several ways and some of the more likely methods are described. While a useful product is readily possible even without such correction factors, a premium product may include the correction factor capability. Tissue contact angle ($\theta_3$) detection methods include the following three approaches.

(1) The first is $\theta_3$ from an Ensite™ (http://www.sjmprofessional.com/Products/US/Mapping-and-Visualization/EnSite-System.aspx) or Carto™ (http://www.biosensewebster.com/products/navigation/cartoxp.aspx) cardiac spatial navigation system based on computed or estimated tip angle to the graphically modeled endocardial surface. These systems already create three-dimensional (3-D) graphical displays of cardiac structures and arrhythmias and enable the spatial navigation of electrophysiology catheters in real time. Such systems already visually and mathematically provide the spatial orientation of the electrode tip and the spatial map and shape of the heart/tissue wall. By either simply observing the display where the RF electrode touches the wall and visually estimating the angle or by adding a simple angle computation utilizing the tip orientation and a computed local wall tangent derived from the wall model, one could obtain the tissue contact angle $\theta_3$.

(2) Most modern catheters have radiopaque markers of gold or other heavy metal routinely used to discern in X-Ray fluoroscopy the position and orientation of a catheter tip such as 1a and sometimes even of a flexible lumen portion such as 1b. Using such conventional markers, the user can already visually discern the approximate tip orientation with respect to the contacting tissue and hence estimate the angle $\theta_3$. As is also widely known, one may additionally utilize an X-Ray contrast agent released into the blood from the catheter to enhance the outline of the blood filled chambers and the heart wall.

(3) The third is the angle $\theta_3$ estimated from a force/angle sensor such as an Enclosense™ force/angle sensor (www.enclosense.com). Such catheter tips as that of Enclosense's "Tacticath"® already report their contact angle and contact force for other purposes of obtaining reproducible ablations. By mounting our inventive transducer in such a tip, one thereby obtains the tissue contact angle $\theta_3$ as well as the tip contact force.

Figure 4:
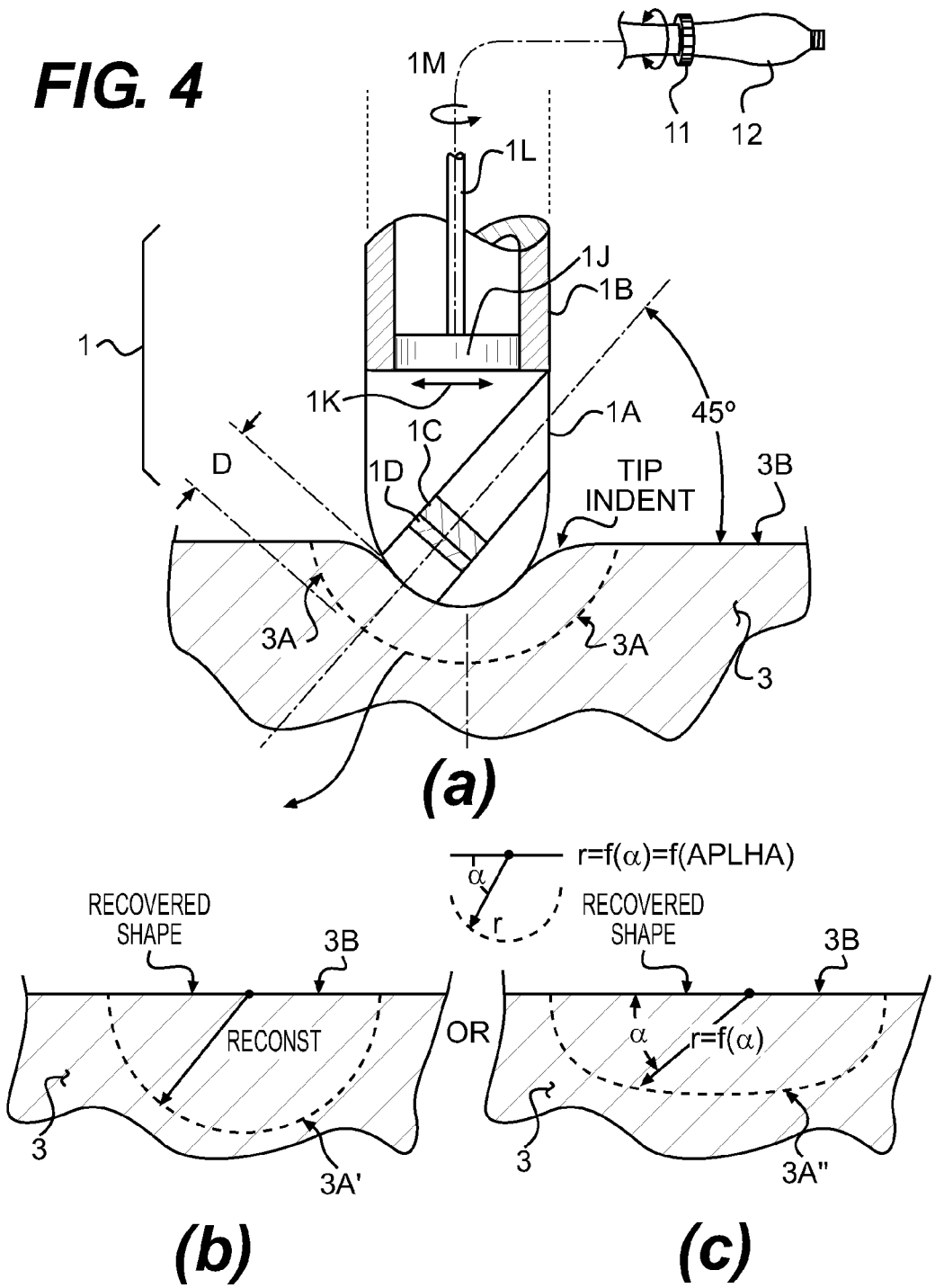
FIG. 4A is a partial sectional view of the ablation tip of FIG. 3 showing an example of a rotation mechanism for rotating the ablation tip and illustrating lesion shapes and depths in the tissue during and after ablation involving contact between the ablation tip and the tissue.
FIG. 4B shows a resulting recovered tissue lesion having a hemispherical shape.
FIG. 4C shows a resulting recovered tissue lesion having a flattened pancake shape.

The actual tissue contact angle $\theta_3$ may be used to correct the ultrasonic lesion depth measurements but it is not always required. FIG. 4 is used to illustrate the reason a correction may be beneficial for maximum lesion-depth accuracy. FIG. 4(a) is a partial sectional view of the ablation tip of FIG. 2 showing an example of a rotational mechanism for selectively rotating the ablation tip itself and illustrating lesion shapes and depths in the tissue during and after ablation involving contact between the ablation tip and the tissue. In FIG. 4(a), the catheter tip 1a is oriented at about 90 degrees to the tissue surface 3b. The transducer 1c/1d and ultrasonic beam path are therefore oriented at about 45 degrees to the tissue surface 3b. The tissue is also typically somewhat indented by the pressing catheter tip 1a. A lesion 3a of depth d (measured in the indented state) as measured along the beam line has been formed by the tissue indenting tip. It will be apparent that, due both to the recovery of the indentation after the tip 1a is physically removed and the lesion's not necessarily having a constant radius (even as indented), the resulting recovered tissue lesion may have a shape ranging between hemispherical (FIG. 4(b) having lesion 3a') and a flattened pancake shape (FIG. 4(c) having lesion 3a''), for example. However we can generally describe the lesion in spherical or polar coordinates as having a variable radius which is a function of at least one angle α measured with respect to a first reference line on the tissue surface 3b (line on paper in FIG. 4(c)), i.e., r=f1(α), as seen in FIG. 4(c). For a hemispherical lesion, the radius is r=constant. Lesions made near 90 degrees (FIG. 4(a)) are typically bodies of revolution and rotationally symmetrical to the tip 1a, whereas if the tissue contact angle $\theta_3$ leans over more toward 45 degrees or less, the lesion starts to become more asymmetrical and no longer a body of revolution as the tip sidewall also starts ablating tissue as well as some of the tip end. By making lesions at various tissue contact angles $\theta_3$, RF powers, times, and irrigant flow rates in the engineering development phase, one can determine the function f1(α) (FIG. 4(c)) for each such set of conditions. Such shape and size behavior data may be provided in or to the ablation catheter from lookup tables or by computational models operated resident on the ablation console or on a network, for example. Note that for an asymmetrical lesion, the lesion radius sampled across the orthogonal lesion length and width cross sections respectively will be a function of two angles f3(α, β), wherein β is measured with respect to a second reference line on the tissue surface 3b which is perpendicular to the first reference line (line into paper in FIG. 4(c)). We have already mentioned above that for maximal convenience, the lesion models can be saved as approximations of the lab data having constant aspect ratios whose overall size is scaled.

We show a 45 degree γ (transducer to tip angle) in FIG. 4. We show a $\theta_3$ (tip to tissue angle) of about 30 degrees in FIG. 3 and 90 degrees in FIG. 4. The actual ultrasonic beam tissue penetration angle (actual tissue beam angle) relative to the tissue normal (ignoring signs) in FIG. 3 is about 15 degrees off normal (90−45−30=15) and in FIG. 4 is about 45 degrees off normal (90−45−90=−45).

Knowing the tissue beam angle (relative to the tissue normal) through a lesion made with a known tip orientation allows, based on prior lesion characterization during product development, the reporting of lesion radius or depth across the two orthogonal planes or sections f1(α) and f2(β). It will be appreciated that f1(α) and f2(β) are generally similar functions for the depicted 90 degree lesion of FIG. 2 but can be dissimilar functions or asymmetric for an ablating tip 1a at a lower than 90 degrees acute angle, as would be anticipated for an RF electrode making a "somewhat sideways" lesion in FIG. 1. It will further be recognized then that even when the tip 1a takes various angles to the tissue surface 3b in FIG. 4, as long as one knows the tissue contact angle $\theta_3$, then one can compute or "look up" the maximum penetrating orthogonal depth of that lesion using f1(α) and f2(β) even though it may likely not occur directly in front of the transducer. Given the ultrasonically measured depth d along the angle α in FIG. 4c and the known tip orientation, one can compute the maximum lesion depth d-max using f1(α) and f2(β) and can also report its length, width, and/or volume. That is because we know at least one detected d along a beamline, know the angle of the beamline (which gives a specific f(α,β) for that setup), and thus one can use f(α, β) and d to compute the maximum depth d-max at whatever angle it occurs as characterized in the engineering lab and provided as computational models and/or lookup tables. Essentially one plugs d into f(α, β) which scales the model to the right size and then reports d-max (at the different angles where d-max is known to occur from prior characterization). Again, we emphasize that these corrections are to obtain maximal accuracy and are not always necessary.

FIG. 3 shows that the transducer 5a/5b is stood-off from the deformed or indented tissue wall 2c by an acoustic standoff 5c which is a low-loss acoustic window material 1 such as urethane, TPX, polystyrene, Ultem® (an unfilled polyetherimide), silicone, or even water or blood. The standoff material fills a cavity 5c having a length s, and may also serve a focusing function in the known manner if desired (i.e., an acoustic lens). This standoff 5c allows detection of shallow lesions of small depth d (e.g., in the 1 mm depth range or less) close to the transducer face despite known nearfield acoustic reverberations of tissue contacting transducers. Further, the transducer 5a/5b is acoustically and mechanically backed by an acoustic attenuation backer material 5d as is known for good quality pulse-echo transducers. High acoustic impedance backers typically contain epoxy or rubber and tungsten while low acoustic impedance backers typically contain epoxy and alumina or glass filler. Either would be highly attenuative as is known in the art, thereby attenuating the backwards propagating waves by about 20-40 dB. The backer material is placed in a cavity 5d, which may be filled with at least (a) an attenuative backing material, and possibly also (b) an electronic circuit such as an amplifier or matching circuit, and/or c) a sensor such as a temperature, spatial positioning or force sensor. The cavity 5d has an angled outer surface (relative to the transducer beam axis 6 and this also favorably discourages multiple acoustic reverberations in the backer material. Thus, the attenuative backer material preferably has a shape conducive to reflection minimization in addition to being an attenuative material.

As mentioned above, the transducer typically and preferably has at least one acoustic matching layer, and at least one acoustic backer material entity. The transducer may utilize at least one of: a single crystal piezomaterial, a polycrystalline piezomaterial, a composite piezomaterial, a CMUT (capacitive micromechanical ultrasound transducer) or other MEMS (microelectromechanical systems) based transducer, and a piezopolymer as is known in the transducer arts. The ultrasonic transducer typically operates somewhere in the range of about 3 megahertz to about 60 megahertz, preferably about 6 megahertz to about 40 megahertz, and more preferably about 8 megahertz to about 25 megahertz. The transducer may have a natural focus distance without using any acoustic lens. Alternatively, an acoustic lens such as a spherical lens (or an acoustic focused or unfocused mirror) is provided for the transducer in the tip. As a lens example, the standoff in FIG. 3 could also act to focus or defocus the beam as long as the material making up the standoff has a velocity different from the velocity of the tissue and the interface between the lens/standoff and the tissue is curved as shown. For instance, a low attenuation unfilled epoxy could serve as both a curved lens and a standoff, as is widely known in the art. An acoustic minor may be used which merely changes the direction of the beam before tip emanation or both reflects/redirects the beam and focuses/defocuses the beam by being a curved minor. The beam angle $\gamma$ is that to the longitudinal tip axis regardless of whether a mirror is used to redirect the beam or not. Further examples include any lens causing the acoustic beam to have a desirable divergence or convergence angle or collimated zero-divergence/convergence angle, and any minor at least redirecting the beam and possibly also, via use of a shaped nonflat minor, causing the acoustic beam to have a desirable divergence or convergence angle or collimated zero-divergence/convergence angle.

As seen in FIG. 3, the transducer 5a/5b is emitting and receiving pings and echoes therefrom and thereto along the beam axis 6. As is known for small disc transducers such as the one shown, there may be a natural focus at 6a even without the use of an acoustic lens 5c. It will be appreciated that the acoustic transmit/receive beam directed along the beam axis 6 will always penetrate lesions made substantially sideways (such as lesion 4c in FIG. 3) as well as lesions made forwardly (see, e.g., FIG. 2) provided the transducer beam axis 6 is rotated toward the tissue surface 2c about the tip long axis.

The transducer mounting angle $\gamma$ relative to its immediate surrounding RF electrode 1a is typically fixed, such as at the approximate 45 degree angle as shown in FIGS. 3 and 4 for the rigid metal electrode tip 1a. In some embodiments, while the electrode tip 1a is preferably rigid in the region immediately around the transducer, the remaining portion of the tip 1a may be flexible, preferably bendably and/or axially flexible. This can be achieved, for instance, by lasering an array of circumferential or helical slots into the walls of a hollow tubular metal tip. See, e.g., U.S. Patent Application Publication No. 2010/0152731. The transducer herein could be placed, for example, at the end of such a flexible metal ablator tip, thereby allowing tip-bending to reorient the transducer relative to tissue (and relative to the catheter body lumen 1b) while still being fixed relative to its immediately surrounding preferably inflexible tip portion.

The transducer is used to make any one or more of the following acoustic measurements along and/or from the direction of the beam: lesion depth along the beamline, proximity to target tissue from a blood pool standoff position, detection of prepopping and popping related phenomenon, and detection of or proximity to anatomical targets to be avoided. As explained the measurement may then optionally be corrected using models or look-up tables and a known tip/tissue beam contact angle for maximal accuracy. The ultrasonic transducer can be operated while RF ablation is active or inactive but preferably the transducer operates during multiple very short pauses in RF ablation (i.e., pinging is interleaved with ablation). "Very short" means short enough that significant tissue cooling does not occur, such as for pauses on the order of milliseconds to a fraction of a second. Typically tens if not hundreds or thousands of acoustic feedback detections are made over the period of a heartbeat. Some may be repeated to reduce signal noise. In one preferred case, ultrasonic measurements are time-interleaved with periods of RF ablation so as to monitor real-time ablating action while also avoiding RF ablation interference into the acoustic measurements. One may also or alternatively carry out before-lesioning and after-lesioning measurements to establish a reflection baseline or to let microbubbles in the nearfield which limit ultrasonic penetration to naturally be reduced upon cooling. In specific situations, at least one acoustic detection is made in a timed relationship with a heartbeat or ECG signal. That is to say, for example, ultrasonic measurements are done preferably at least at the same phase point in the heartbeat for all heartbeats. Similar synchronized measurements may also be done at other cyclic phases of the heartbeat and/or the breathing pattern. During a given heartbeat cycle when tissues are moving, the tip-tissue contact angle $\theta_3$ and tip contact force will cyclically vary and angular variation can be taken into account by recognizing that the varying angles result in slightly different detected depths for each such instantaneous orientation.

The duty cycle of the ultrasonic transducer's operation is preferably less than about 20%, more preferably less than about 10%, and most preferably less than about 5%. In one embodiment, the on-time for an individual ultrasonic measurement period is equal to or less than a thermal time constant of the cooling tissue which assures that only minimal cooling takes place between the RF power-off and following RF power-on events. In other embodiments, the ultrasonic on-time is preferably less than about 0.15 seconds or 150 milliseconds, more preferably less than about 0.10 seconds or 100 milliseconds, and most preferably less than about 0.05 seconds or 50 milliseconds per individual measurement period during which one or more pulse-echo events take place.

The catheter body and/or tip may further include any one or more of the following known components: a thermistor or thermocouple, an irrigation and/or suction lumen, a spatial position sensor (as for the prior mentioned Ensite™ or Carto™ systems), a contact-force sensor, part or all of a tip contact angle to tissue sensor of any type, a platinum, gold, or rhodium metal or alloy electrode component or radiopaque member, and a metallic thin film or mesh electrode in an acoustic pulse-echo path. The thin film or mesh allows the face of the transducer itself to also optionally act as an acoustically transparent yet electrically ablating RF electrode.

A solid metal RF electrode tip $1a$ would be drilled out or otherwise provided with a bore to allow beam passage and placement of the transducer and the optional window, lens or standoff. If the standoff is electrically insulating, then that portion of the tip will not cause RF ablation unless it is overcoated with a metal film or foil. Within the scope of the invention is the provision of a metal coated or otherwise electrically conductive ultrasonic component(s) such as the standoff, lens, or matching layer such that this drilled-out region still is capable of delivering RF ablation power even across the face of the underlying standoff and/or lens. The inventors have found that even if the acoustic element face is not providing RF ablation, the nearby remaining tip metal periphery still forms a lesion similar to that of a standard non-drilled tip. The inventors believe that this is because as long as one has a circular donut-shaped electrode contact area to tissue, the RF current density at any appreciable tissue depth is relatively unchanged from that of a solid electrode. The tissue close to and immediately in front of the electrically insulating standoff/lens $1e$ is backfilled and sideways-filled with heat generated deeper in front of the tip and adjacently at the metallic periphery of the metallic hole in the tip. The astute reader will recognize that if the RF ablation electrode and the matching layer are electrically connected and both conductive, then the operation of the transducer and the operation of the RF ablation are no longer independent. Although we do not intend to teach specific electrical circuits, it will quickly be recognized that one can simply short the transducer across its thickness during RF ablation using a switch at the handle end of the catheter. That prevents the transducer from interfering with RF power delivery and likewise prevents transducer operation causing ablation electrode excitation.

The inventors have also found that by placing the thin metal film over the acoustic element to also provide RF ablation from the beam emission area, they can reduce the maximum RF power density otherwise occurring at the peripheral circumferential edge of the cored electrode which inhibits early bubble formation.

The RF ablation catheter has a single ultrasonic pulse-echo transducer in the RF ablating tip used for pulse-echo lesion feedback. The transducer beam's centroid is oriented at approximately 30-60 degrees to the catheter tip longitudinal axis such that it has at least some view of lesions being made in any FIG. 3 catheter-to-tissue orientation $\theta_3$. If the ultrasonic beam, for example, has a somewhat diverging beam within the lesioned region, then it "covers" a wider range of angles than a narrower beam for given transducer angle $\gamma$ and tissue contact angle $\theta_3$ and will report an average lesion depth $d_3$ for that divergent angle range presuming no effort is made to discern the closer reflections from the deeper reflections. We again stress that the 30-60 degrees is the beam emanation angle relative to the surrounding tip longitudinal axis regardless of whether the transducer is used with or without an acoustic mirror which internally redirects the beam before tip emanation.

The catheter 1 (or the catheter tip $1a$ alone in FIG. 4$a$) is manually or automatically rotated about the longitudinal tip axis such that the transducer beam faces the indented tissue 3 as directly (as near normal) as possible for measurement of the lesion depth d along the beam. This orientation also typically results in the maximum acoustic reflected energy from depth and the maximized signal/noise performance. Alternatively, one may measure the depth d at a variety of tip-to-tissue orientations during or after local lesioning is tentatively finished.

Referring again to FIG. 4($a$), the electrode tip $1a$ may be rotated relative to catheter body $1b$ such as upon a bearing member $1j$. A rotational drive shaft $1l$ is used to rotate around the longitudinal axis in an axial rotational direction $1m$ to impart rotation $1k$ upon the tip $1a$ relative to the nonrotating catheter body $1b$. The drive shaft $1l$ could be replaced with an in-tip motor or some other in-tip powered actuator. Alternatively, and as widely known in the rotational catheter art, one may bodily rotate the entire catheter $1a/1b$ wherein the tip $1a$ does not rotate relative to the body $1b$ but is fixed relative to the body $1b$. Such bodily rotation is now routinely done by the practitioner manually rotating a rotational control member 11 of a proximal catheter handle 12. As is also known, catheter 1 may be bodily rotated in that manner while residing in a stationary introducer surrounding sheath 91 which provides a slippery bearing surface around the catheter 1 and may have its own steering wires. An advantage of the approach using the rotational bearing $1j$ of FIG. 4($a$) is that one gets rotation without requiring a larger overall catheter or catheter/sheath diameter or French size. If one instead (or in addition) uses the sheath, then one now is introducing a larger sheath into the lumen and may be more restricted in access. However, the inventors have had good results using a 7 French ablation catheter in sheaths designed to accept the 7 French ablation catheter.

An important aspect of the present invention is that a lesion's shape and specific size (actual depth and aspect ratios) are primarily a function of power, cooling, force, and contact angle. In general for a given set of these parameters, one obtains highly similar lesions in terms of their three dimensional shapes (i.e., aspect ratios) even as their absolute sizes increase during growth. The pinger transducer $5a/5b$ of FIG. 3 provides the actual instantaneous lesion depth along beam axis 6 regardless of how the parameters are set. Given the beam axis actual "lesion depth" from the transducer which in general is not 90 degrees to the local tissue, the following summarizes the three above-described examples of how to estimate the actual maximum lesion depth roughly orthogonal (i.e., 90 degrees) to the compressed contacted tissue centroid point. First, as a rough estimate, one can simply use the uncorrected beamline depth as an approximation of the lesion's true orthogonally penetrating d-max. Second, as a finer estimate, one can utilize the practitioner's estimate of actual contact angle such as that determined by fluoroscopy or the like. This might even be done with automatic feedback from the x-ray equipment. Knowing the angle and any information relating to how depth varies by angle for particular lesion situations (such as with a lesion model for the given contact angle), one can correct for the orthogonal maximum depth. Third, a preferred approach utilizes the tip contact angle feedback as provided by a 3D chamber modeling and navigation system, such as the Ensite™ products of St. Jude Medical and the Carto™ products of Biosense Webster. This could be done transparent to the practitioner. This third approach can actually utilize data from any available angle-sensing sensor onboard the tip, not just the graphical based systems mentioned. This lesion depth correction is performed by a lesion depth correction module described below (see FIG. 5).

The basic steps for true 90 degrees-to-contacted tissue lesion depth d-max determination are as follows: (a) obtain before and after lesioning pinged echoes (which may also include interleaved measurements); (b) looking at differences in the pinged echoes as lesioning proceeded (or has tentatively finished), determine the projected lesion depth d-beamline along the pinger beam axis 6 of FIG. 3; (c) do one of the following: (i) assume a nominal contact angle estimate or measure a contact angle using imaging means such as fluoroscopy as described above, (ii) automatically compute a contact angle using a 3D navigation/chamber modeling system as described above; and (d) report (or provide feedback regarding) the actual maximum lesion depth d-max orthogonal to the contacted tissue surface which is obtained via a model of a typical lesion made under those conditions (at that contact angle) wherein d-beamline is employed to scale the fixed proportions model to the correct size and then d-max is computed and reported at its known orthogonal position using the scaled model.

Figure 5:
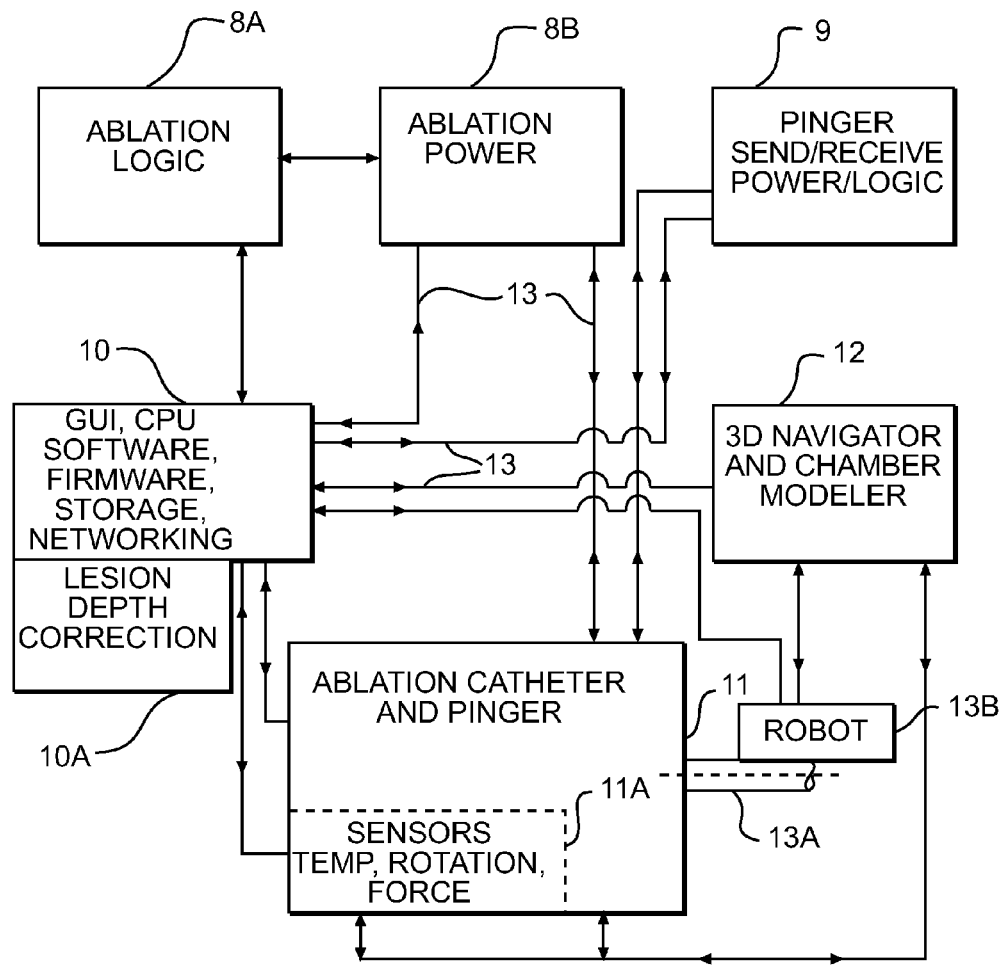
FIG. 5 shows a schematic block diagram of an ablation system incorporating the acoustic feedback catheter of FIG. 3.

FIG. 5 shows a schematic block diagram of an ablation system incorporating the inventive acoustic feedback catheter and supporting hardware and software. The major components include ablation logic unit 8a, ablation power unit 8b, pinger send/receive power/logic unit 9, GUI, CPU, software, firmware, storage and networking unit 10, and ablation catheter with sensing transducer 11, optional 3D navigation/modeling system unit 12, optional catheter manipulation robot 13a/b, and a variety of lines 13 for passage of data, power, logic, coolant, and the like.

The ablation logic unit 8a includes logic circuitry to power and control ablation, which can be TTL (Transistor-Transistor Logic), gate arrays, or even software. The ablation power unit 8b includes the actual power source for ablation. In addition to RF, other ablation energy sources may be employed including lasers, cryo, RF bipolar, RF unipolar, microwave, HIFU (High Intensity Focused Ultrasound), and electroporation. Such power supplies are usually accompanied by a supply cooling mechanisms. The pinger send/receive power/logic unit 9 includes the pinging transmit powering and receiving circuitry and logic for the transducer pinger. On the transmit side it is capable of sending short pulses or pulse trains at an operating frequency. On the receive side it senses the voltage waveforms induced by returning echoes, possibly incorporating amplification, noise reduction, and electrical-matching.

The GUI, CPU, software, firmware, storage and networking unit 10 is also referred to as the control and interface system 10. It includes a graphical user interface (GUI), firmware for system operation, storage/memory for system operation, and networking interfaces. The GUI may include any one or more of a display, a touch screen, a keyboard, a computer mouse, and the like. If the optional robotic subsystem 13a/b and/or navigation system 12 are also employed, then the user GUI may be used on those subsystem(s) as well. Software in the ablation system can run on the CPU in the control and interface system 10; however, some amount of software/firmware may also be distributed within the individual modules or units in the ablation system of FIG. 5. Patient information is stored in the storage/memory and a network interface to the hospital network is provided in the control and interface system 10. The control and interface system 10 is configured or programmed to process transducer detection information from the pulse-echo ultrasonic transducer and to provide feedback to a user via the GUI and as internal system feedback to be used to control ablation by the ablation tip. The control and interface system 10 includes a lesion depth correction module 10A, in the form of hardware or software or firmware, for performing the lesion depth correction described above, to convert the detected lesion depth along the beam direction to a corrected lesion depth in a normal direction which is perpendicular to the tissue surface 2c in contact with the ablation tip 1a. The control and interface system 10 is coupled to the rotation mechanism to rotate the distal tip preferably in order to achieve as near an orthogonal tip-to-tissue contact as possible. The control system 10 may also include prepop or popping detection software. During lesioning, the inventive system may also supplement the acoustic feedback with known electrical impedance feedback or ECG feedback (not shown) for even better control.

The ablation catheter with sensing transducer 11 includes, preferably, a disposable acoustic feedback ablation catheter with the pinger transducer such as that shown in FIG. 3 or 4. This invention is not limited to the single transducer shown in FIG. 1, but may provide dual transducers or the like. The ablation catheter 11 may also include one or more of a variety of known sensors 11a that may be resident in/on or coupled to the ablation tip, such as temperature sensors, tip-rotation sensors, tissue contact force or angle sensors, blood flow or pressure sensors, IVUS or OCT imaging transducers or elements and navigation sensors. The inventors have herein described the single transducer as having a fixed angle γ (FIG. 3). Within the scope of "fixed angle" is a rotating transducer or transducer tip (such as that of FIG. 4 or of a rotating IVUS transducer) wherein the transducer is rotated about the tip axis manually, automatically, intermittently or continuously thereby providing measured depths d-beamline over a range of angles. It will be appreciated that those angles relative to the tip longitudinal axis are also in a fixed relationship. We again mention that the ablation catheter may be employed from within a sheath 91 such as a steerable Agilis™ sheath.

The optional 3D navigation/modeling system unit 12 includes, for example, the Ensite™/NavX™ system from St. Jude Medical or the Carto™ system from Biosense-Webster for 3D spatial navigation and/or surface modeling. It is capable of automatically calculating and providing the transducer tip contact angle to tissue utilizing system software without user involvement. Alternatively the contact angle can be eyeballed from the navigator GUI. The optional catheter manipulation robot 13a/b is a robot which can manipulate the catheter 11 thus reducing x-ray exposure of the practitioner or allowing for remote procedures. The lines 13 allow passage of electrical power, data, logic signals, ping receive signals, ping transmit signals, and any required coolant between the various system units and/or catheter.

Figure 6:
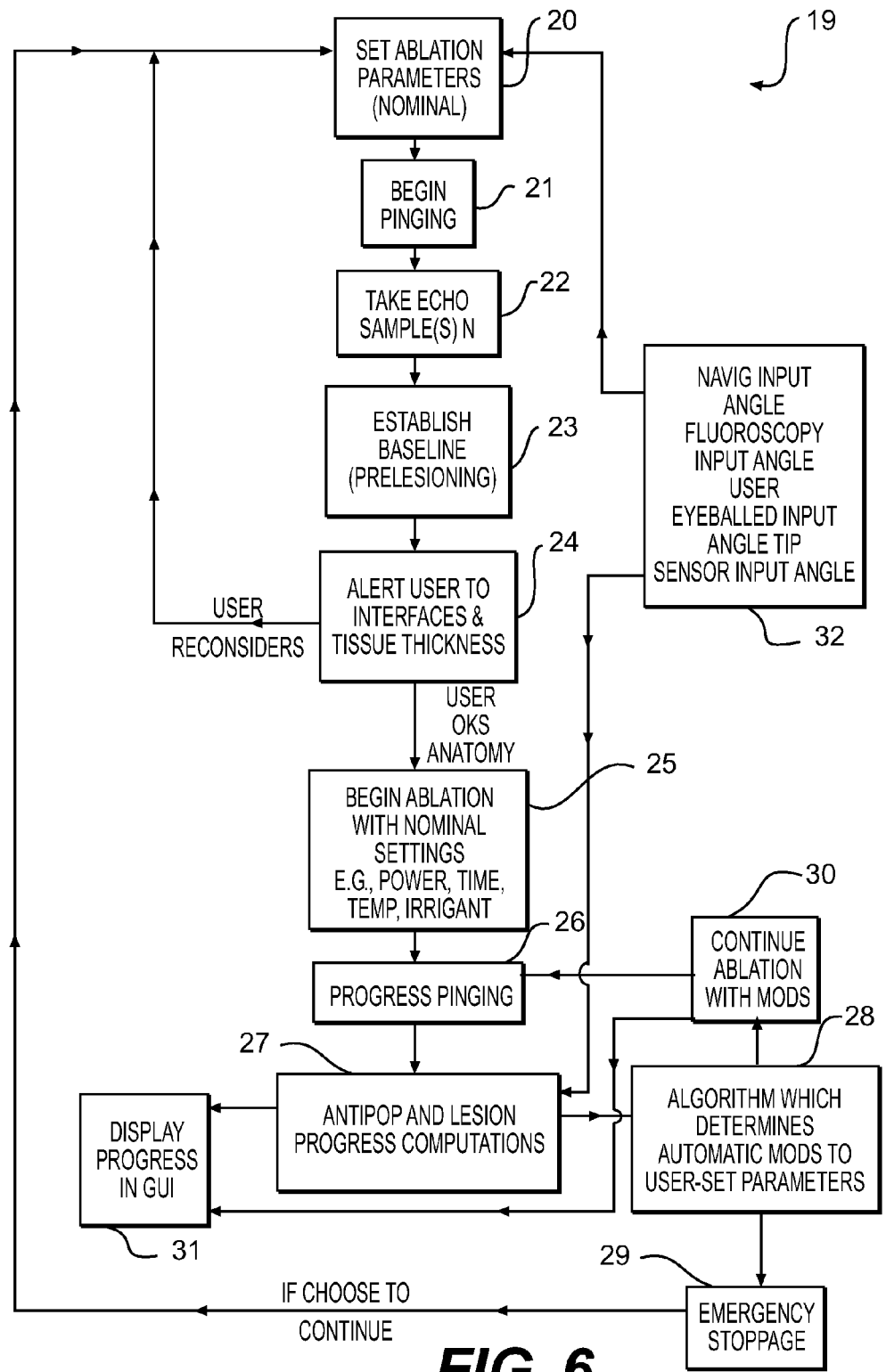
FIG. 6 shows a flow diagram illustrating the logic and decision-making employed by the hardware and software of the ablation system of FIG. 5.

FIG. 6 shows a flow diagram illustrating the logic and decision-making employed by the hardware and software of the ablation system of FIG. 5, which depicts a functional block diagram of a representative physical system implementation. The major sections of the diagram are a setup loop (upper loop blocks 20-24 and 32) wherein the user inputs the ablation parameters and selects an ablation site and a lesioning loop (lower loop blocks 25,26,27,28, 30, 31) wherein the ablation is carried out with an awareness of pinging feedback. Specifically, a start block 20 is where a user inputs one or more requested lesion parameters such as one or more of a lesion dimension or volume, an RF power or time, a maximum temperature, or an irrigant flow rate. At the same time, at block 20 the catheter model number is manually or automatically inputted. At the same time, the system itself receives from block 32 any available tip contact angle, contact force, contact impedance and lesion models.

At block 21, continuous pinging begins and at subsequent block 22 (take echo sample(s) N) and block 23 (establish baseline (pre-lesioning)), the pinger is continuously operated while the doctor chooses a lesioning target. At block 24, the pinging echoes are analyzed and reported such as to carry out any one or more of (i) warning of in-range interfaces and (ii) advising that tissue contact is good or bad. Subsequently, the user gives the go-ahead for lesioning or commands the system to stop such that setup can be repeated at block 20 at a different site or coupling/contact situation.

Presuming the user or doctor gives the go signal at block 24, the baseline prelesion pinged echo from the intended target site is saved at block 24 as a starting reference for later comparison before proceeding to block 25. At the next block 25, ablation begins with the inputted settings of block 20 (e.g., nominal settings such as power, time, temperature, and irrigant). The next block 26 depicts pinging for lesion progress monitoring, the pinged data results then being employed in following block 27 to determine a lesion state and/or pop risk. Then, block 28 evaluates whether any power, flow or other lesioning parameters should be adjusted (automatic modifications to user-set parameters) depending on whether the lesion state of block 27 was determined as on-plan or safe or as off-plan or unsafe. Next, block 30 shows such adjustments (if any) being applied followed by a subsequent return to block 26 for continued progress pinging under the adjusted lesioning parameters. As an alternative to applying adjustments at block 30, the system may determine that an emergency shutdown is necessary at block 29 because no adjustment can recover the desired behavior; however, this outcome is preferably avoided by having the feedback and adjustments discussed above. We note that the lesioning loop may be passed through dozens or hundreds of times during an ablation.

The lesioning status is thus reported both to the system itself (block 27 to 28) and to the GUI (block 27 to 31). Note that the optional sources of contact angle, contact force, contact impedance and lesion/prepop models of block 32 may also be provided to block 27 during lesioning if they have changed.

The inventors note that it is preferable to ping at least every second or so if not much more often (but still at the low duty cycle discussed previously) so as to avoid having the system being surprised by a large or unsafe change in lesion progress or pop risk. In particular we know that changes to lesioning parameters at block 28 must be applied as early and as often as possible so as to avoid ever getting into a serious pop state. The "algorithm" is software (or firmware) applied particularly at blocks 27 and 28 which is used to (a) quantify a lesion state and/or a pop risk and (b) compare it to a desired state and/or risk and make ablation adjustments if needed such as an ablative power reduction. Such algorithms can take several forms. Two preferred algorithm features are discussed herein below.

The first feature is a pop avoidance portion of code which essentially looks for excessive ping reflections or excessive ping reflection growth rates in the lesioning field, but most particularly in the 1-3 mm range whereat the hotspot is known to occur for irrigated RF catheters. Reflected echoes are caused by both microbubble formation in the tissue and by actual protein cross-linking of the tissue. The inventors have found that when an undesirable nearfield hotspot prepop bubble cloud gets dense enough (acoustically opaque), one can no longer see echoes coming from behind it (from deeper). This is a sure sign of a potential pop and what needs to be done is to reduce the temperature increase rate and peak temperature otherwise reached in the prepop region. That can be done, for example, by throttling RF ablation power (on/off, proportional control etc) and/or by increasing irrigant flow at blocks 28/30.

The second feature is a lesion progress portion of the code which looks for a minimum desired strength of reflection from tissue thought to be indicative of complete lesioning or necrosis. That is, the looked-for level of pinged reflection is reached when a microbubble or other contrast has increased to a level known (via engineering characterization during product development) to correlate to fully lesioned or necrosed tissue. Lower levels indicate partially lesioned tissue. For example, fully lesioned tissue might have a reflectivity 20, 30 or 40 Db above the prelesioned level at a particular depth. Another way to state this is that one looks for what portion of the ingoing beam is reflected from which depths. Higher reflections indicate more lesioning damage. For example, if half or three quarters of the ingoing beam is newly reflected after some lesioning from a distributed depth, then it will be obvious that substantial reflectors indicative of microbubbles and protein-crosslinking have occurred through a depth-range and that the strong reflection is not just a localized (in depth) prepop bubble cloud. It should be apparent that by establishing a ping prelesion baseline, we can account for (prelesion) tissue differences from spot to spot and thereby only consider ping reflection changes relative to that specific baseline.

Those familiar with pulse-echo work know that deeper features are harder to see because nearer field features can obstruct (mask) the deeper ones. The inventors have found that excessive nearfield microbubbling of the extent indicative of an impending pop masks deeper lesioning making progress-monitoring of deeper lesions more difficult. There are a few solutions to this as follows. First, one can always operate the tip such that nearfield reflections stay under a maximum value which is below the excessive masking level and the level known to lead to pops. This can be done by one or both of irrigant flow adjustments (higher flows) and RF power adjustments (lower average power). Second, one can use longer delays between RF ablative power pulses and constant cooling thereby allowing more nearfield cooling. Third, one can selectively precool the nearfield as with cooled water irrigant (lower than 37 Deg C. body temp) using pulsed or continuous RF ablation, preferably pulsed. In this case, the irrigant pump may become a combined pump and water-cooler.

Of course, the system configuration illustrated in FIG. 5 is purely exemplary of systems in which the present invention may be implemented, and the invention is not limited to a particular hardware or software configuration. The computers and storage systems implementing the invention can also have known I/O devices (e.g., CD and DVD drives, floppy disk drives, hard drives, etc.) which can store and read the modules, programs and data structures used to implement the above-described invention. These modules, programs and data structures can be encoded on such computer-readable media. For example, the data structures of the invention can be stored on computer-readable media independently of one or more computer-readable media on which reside the programs used in the invention. The components of the system can be interconnected by any form or medium of digital data communication, e.g., a communication network. Examples of communication networks include local area networks, wide area networks, e.g., the Internet, wireless networks, storage area networks, and the like.

The inventive system's ability to detect lesion progress may be employed to simply inform the user to manually adjust parameters and/or may be used in a closed loop configuration wherein the system itself adjusts its own parameters as the lesioning progresses. The inventors anticipate that at least the prepop feedback will utilize a system feedback loop since a human user cannot react as fast as a computer to an unsafe condition.

FIG. 7 is a partial sectional view of an RF ablation tip wherein the transducer itself is forward pointing but its beam is redirected sideways by an acoustic minor before exiting the ablation tip. The acoustic mirror is employed to redirect the beam out of the tip. FIG. 7 shows a catheter 61 with a minor-based tip electrode 61a and a polymer catheter body 61b. The catheter 61 is immersed within a blood pool 63 for forming a lesion 64d in endocardial tissue 62a. The catheter tip as shown has two metallic or electrically conducting parts: a rigid part 61a and a flexing part 61a' having flexure slots 61a". The rigid tip portion 61a contains a transducer again comprised of a matching layer 65b, a piezocrystal 65a, and an acoustic backer 65d. Note that in the tip electrode 61a of FIG. 7, the transducer is forward facing and emits its beam in the distal −X direction. Note further that the tip electrode 61a contains an acoustic minor 84 which redirects the outgoing and incoming beam 90 degrees to the longitudinal tip axis. The acoustic path between the minor 84 and transducer 65b, a,d is filled with saline 65c'. The saline 65c' serves as an acoustic standoff from the tissue surface 62c such that the first couple of millimeters of tissue depth can be seen without interfering transducer ringdown artifacts. The minor 84 would likely be of stainless steel or tungsten but could alternatively be of an air-like material such as a glass microballoon filled epoxy. A tip aperture or orifice 85 is provided at the beampath 66/66a such that the acoustic beam does not collide with the tip housing. Presuming the tip electrode 61a is an RF ablation electrode, then the tip container or shell would likely be formed of metal such as platinum-iridium in the known manner. The aperture or beam-orifice 85 is depicted as an open hole. In this manner, saline pumped into the tip cavity 65c' exits the orifice 85. Some smaller amount of saline may exit small laser-drilled holes (not shown) separate from the orifice 85. Note that by having the majority of the saline exiting the tip orifice 85, the tip electrode around the orifice is well-cooled despite its having a high RF-current density around its orifice perimeter. Further, the emanating saline serves to acoustically couple the transducer to the tissue and prevents bubbles from becoming trapped in or near chamber 65c' or aperture 85.

The inventors specifically note that if one monitors the water pressure being applied to the tip from outside the patient, one can easily tell when the aperture 85 (and therefore the acoustic beam) is facing the tissue squarely because the back-pressure increases when the aperture is sealed against the tissue. This pressure monitoring technique can be employed manually or automatically to achieve tip-aiming and can be done so independently or in combination with observing the actual acoustic pinging feedback.

The acoustic minor 84 may, for example, have an angle of 45 degrees resulting in a 90 degree beam exit (shown) or a different angle such as 22.5 degrees resulting in a 45 degree beam exit (not shown). The minor thickness need only be thick enough to provide adequate reflection (e.g., 95% or better) and for metals this is actually quite thin (on the order of microns thick). For manufacturing convenience, the mirror 84 can be thicker and all metal as shown in FIG. 7 or alternatively could comprise micromolded polymer having a thin-film metallic coating.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. For example, the tip electrode may also serve as a sensing or pacing electrode. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation system comprising:
   a catheter including an elongated catheter body extending longitudinally between a proximal end and a distal end along a longitudinal axis, and at least one ablation element disposed in a distal portion which is adjacent the distal end of the catheter body to ablate a targeted tissue region outside the catheter body by contacting a tissue surface;
   a pulse-echo ultrasonic transducer disposed in the distal portion and arranged to emit and receive an acoustic beam having a centroid along a beam axis direction at a transducer angle of between about 30 degrees and about 60 degrees relative to a distal direction of the longitudinal axis at a location of intersection between the longitudinal axis and the beam direction of the centroid of the acoustic beam, wherein the pulse-echo ultrasonic transducer emits and receives acoustic pulses to provide transducer detected information regarding the targeted tissue region being ablated;
   a rotation mechanism to rotate at least the distal portion around the longitudinal axis; and
   a control and interface system to process the transducer detected information from the pulse-echo ultrasonic transducer and to provide feedback to at least one of a user via a user interface or the control and interface system itself to be used to control ablation by the at least one ablation element;
   wherein the transducer detected information includes a detected lesion depth along a beam emanation direction; and
   wherein the control and interface system includes a lesion depth correction module which converts the detected lesion depth along the beam direction to a corrected lesion depth in a normal direction which is perpendicular to the tissue surface in contact with the at least one ablation element.

2. The ablation system of claim 1,
   wherein the acoustic beam passes into the targeted tissue region from the pulse-echo ultrasonic transducer facing the targeted tissue region in a transducer-facing direction, the acoustic beam has a beam-emanation direction from the pulse-echo ultrasonic transducer, and the beam-emanation direction is the same as the transducer-facing direction.

3. The ablation system of claim 1, further comprising
an acoustic mirror which redirects the acoustic beam from the pulse-echo ultrasonic transducer into the targeted tissue region at a beam-emanation direction;
wherein the pulse-echo ultrasonic transducer faces the acoustic mirror in a transducer-facing direction; and
wherein the beam-emanation direction is different from the transducer-facing direction.

4. The ablation system of claim 3,
wherein the transducer-facing direction is substantially along the longitudinal axis of the distal portion of the catheter and the beam-emanation direction is at an angle relative to the transducer-facing direction.

5. The ablation system of claim 1,
wherein the distal portion has a rigid part.

6. The ablation system of claim 5,
wherein the distal portion has a flexible part coupled between the rigid part and a proximal portion of the elongated catheter body.

7. The ablation system of claim 1,
wherein the rotation mechanism rotates the catheter body including the distal portion as a whole, the rotation being one of manual or robotic or automatic rotation.

8. The ablation system of claim 1,
wherein the rotation mechanism rotates the distal portion relative to a proximal portion of the catheter body, the rotation being one of manual or robotic or automatic rotation.

9. The ablation system of claim 1, further comprising:
a sheath through which the catheter body is introduced to the targeted tissue region;
wherein the rotation mechanism rotates one of the distal portion or the catheter body including the distal portion with respect to the sheath.

10. The ablation system of claim 1, wherein the lesion depth correction module is configured to convert the detected lesion depth along the beam direction to a corrected maximum lesion depth using both (i) a measured or observed tissue contact angle between the tissue surface in contact with the distal portion and the longitudinal axis of the distal portion of the catheter body and (ii) a model or stored description of lesion shapes made under similar ablating conditions using the at least one ablation element, wherein the tissue contact angle is provided by one of:
receiving from a user a visual estimation of the angle;
deriving the angle from an imaging modality for imaging position and orientation of the distal portion;
deriving the angle from a three-dimensional surface modeling system to provide spatial orientation of the distal portion and spatial map and shape of the tissue surface; and
deriving the angle from a contact angle sensor in or adjacent the distal portion.

11. The ablation system of claim 10,
wherein the model or stored description of lesion shapes, which is obtained based on at least two of RF power, RF time, tissue contact angle, and irrigant flow rate, provides a nominally expected lesion shape and size as described by at least one of a maximum depth, a maximum width, a maximum length, or a volume of the lesion.

12. The ablation system of claim 11,
wherein the nominally expected lesion shape is size scaled, using a ratio of the detected lesion depth along the beam direction and a corresponding depth of the nominally expected lesion shape along the beam direction, to obtain a size-scaled lesion shape having the corrected maximum lesion depth.

13. The ablation system of claim 12,
wherein the lesion depth correction module also provides one or more of the maximum length, the maximum width, and the volume of the lesion of the size-scaled lesion shape.

14. The ablation system of claim 1, further comprising:
a robot coupled to the catheter and the rotation mechanism to manipulate the catheter.

15. The ablation system of claim 14,
wherein the control and interface system is coupled to the robot to control the robot using the transducer detection information.

16. The ablation system of claim 1,
wherein the rotation mechanism comprises a proximal catheter handle coupled with the catheter body and the distal portion.

17. The ablation system of claim
wherein the transducer angle is about 45 degrees.

18. The ablation system of claim 1, further comprising:
an ablative energy source to supply ablative energy to the at least one ablation element, the ablative energy source comprising one or more of unipolar RF, bipolar RF, microwave, laser, cryo, infrared, electroporation, and chemicals.

19. The ablation system of claim 1,
wherein the pulse-echo ultrasonic transducer has an operating frequency of between about 3 megahertz and about 60 megahertz.

20. The ablation system of claim 1, wherein the control and interface system is coupled to the pulse-echo ultrasonic transducer to operate the transducer to perform transducer detection at least one of:
before supplying ablative energy to the at least one ablation element;
simultaneously with supplying ablative energy to the at least one ablation element;
while the at least one ablation element is inactive and for time periods that are time-interleaved with supplying ablative energy to the at least one ablation element;
after supplying ablative energy to the at least one ablation element and stopping supply of the ablative energy; and
for multiple acoustic feedback detections over a period of a heartbeat or breath;
for at least one acoustic detection made in a timed relationship with a heartbeat cycle or ECG signal.

21. The ablation system of claim 1,
wherein the control and interface system is coupled to the pulse-echo ultrasonic transducer to operate the transducer to have a duty cycle of less than about 20%.

22. The ablation system of claim 1,
wherein the control and interface system is coupled to the pulse-echo ultrasonic transducer to operate the transducer to provide an on-time for an ultrasonic measurement period that is approximately equal to or less than a thermal time constant of the targeted tissue region with the tissue surface being contacted by the at least one ablation element during cooling of the targeted tissue region.

23. The ablation system of claim 1,
wherein the control and interface system is coupled to the pulse-echo ultrasonic transducer to operate the transducer to provide an on-time for an ultrasonic measurement period that is less than about 0.15 seconds.

24. The ablation system of claim 1, wherein processing the transducer detection information by the control and interface system comprises at least one of:
- determining the corrected lesion depth;
- determining lesion-making progress;
- determining a tissue thickness;
- determining lesion transmurality;
- identifying activity indicative of prepopping or popping;
- determining a rotation state of the distal portion;
- determining a distance from the distal portion to the tissue surface from within a blood pool.

25. The ablation system of claim 1,
wherein the control and interface system is coupled to the rotation mechanism to rotate the distal portion in order to achieve a maximal degree of orthogonality with respect to the tissue surface.

26. The ablation system of claim 1, further comprising:
one of an acoustic standoff and a lens disposed between the pulse-echo acoustic transducer and the targeted tissue region.

27. The ablation system of claim 1, further comprising:
an attenuative backer material having a shape conducive to reflection minimization;
wherein the pulse-echo acoustic transducer is disposed between the attenuative backer material and the targeted tissue region.

28. The ablation system of claim 1,
wherein the pulse-echo acoustic transducer is mounted in a hole in the distal portion and the distal portion comprises an electrically conductive material at least on a surface of the distal portion to deliver RF ablation at least from outside of a region of the transducer beam path.

29. The ablation system of claim 1,
wherein the pulse-echo acoustic transducer is the only acoustic transducer in the catheter.

30. The ablation system of claim 1,
wherein the control and interface system is coupled to the rotation mechanism to rotate the distal portion and to the distal portion to manipulate other movements of the distal portion in order to orient the beam direction to form an angle of between about 0 and about 45 degrees relative to the tissue surface in contact with the at least one ablation element.

31. An ablation system comprising:
a catheter including an elongated catheter body extending longitudinally between a proximal end and a distal end along a longitudinal axis, and at least one ablation element disposed in a distal portion which is adjacent the distal end of the catheter body to ablate a targeted tissue region outside the catheter body by contacting a tissue surface;
a pulse-echo ultrasonic transducer disposed in the distal portion and arranged to emit and receive an acoustic beam having a centroid along a beam axis direction at a transducer angle of between about 30 degree and about 60 degrees relative to a distal direction of the longitudinal axis at a location of intersection between the longitudinal axis and the beam direction of the centroid of the acoustic beam, wherein the pulse-echo ultrasonic transducer emits and receives acoustic pulses to provide transducer detected information regarding the targeted tissue region being ablated;
means for rotating at least the distal portion around the longitudinal axis; and
a control and interface system to process the transducer detected information from the pulse-echo ultrasonic transducer and to provide feedback to at least one of a user via a user interface or the control and interface system itself to be used to control ablation by the at least one ablation element;
wherein the transducer detected information includes a detected lesion depth along a beam emanation direction; and
wherein the control and interface system includes means for converting the detected lesion depth along the beam direction to a corrected lesion depth in a normal direction which is perpendicular to the tissue surface in contact with the at least one ablation element.

\* \* \* \* \*